US012651671B2

(12) United States Patent
Lobsiger et al.

(10) Patent No.: US 12,651,671 B2
(45) Date of Patent: Jun. 9, 2026

(54) TREATMENT PARAMETER ESTIMATION USING ORTHOGNATHIC INFORMATION

(71) Applicant: Align Technology, Inc., San Jose, CA (US)

(72) Inventors: Janik Lobsiger, Schaffhausen (CH); Bernhard Steffen Thomaszewski, Zürich (CH); Daniel Michel Peter, Dürnten (CH); Niko Benjamin Huber, Zug (CH)

(73) Assignee: Align Technology, Inc., San Jose, CA (US)

( * ) Notice: Subject to any disclaimer, the term of this patent is extended or adjusted under 35 U.S.C. 154(b) by 571 days.

(21) Appl. No.: 18/167,797

(22) Filed: Feb. 10, 2023

(65) Prior Publication Data

US 2023/0268079 A1 Aug. 24, 2023

Related U.S. Application Data

(60) Provisional application No. 63/313,145, filed on Feb. 23, 2022.

(51) Int. Cl.
*G16H 50/50* (2018.01)
*A61C 7/00* (2006.01)
(Continued)

(52) U.S. Cl.
CPC ............. *G16H 50/50* (2018.01); *A61C 7/002* (2013.01); *A61C 9/0046* (2013.01); *G06F 30/27* (2020.01);
(Continued)

(58) Field of Classification Search
CPC ........ G16H 20/30; G16H 50/50; G16H 30/40; G16H 50/20; G16H 20/40; A61C 9/0053;
(Continued)

(56) References Cited

U.S. PATENT DOCUMENTS

| | | | |
|---|---|---|---|
| 5,975,893 | A | 11/1999 | Chishti et al. |
| 6,227,850 | B1 | 5/2001 | Chishti et al. |

(Continued)

FOREIGN PATENT DOCUMENTS

| | | |
|---|---|---|
| CN | 113408174 A | 9/2021 |

OTHER PUBLICATIONS

Dorda D, Peter D, Borer D, Huber NB, Sailer I, Gross M, Solenthaler B, Thomaszewski B. Differentiable simulation for outcome-driven orthognathic surgery planning. InComputer Graphics Forum Dec. 2022 (vol. 41, No. 8, pp. 53-61).*

(Continued)

*Primary Examiner* — Phu K Nguyen
(74) *Attorney, Agent, or Firm* — Lowenstein Sandler LLP

(57) ABSTRACT

A method includes receiving a) orthognathic patient data comprising information representing an initial state of a patient and b) plurality of treatment parameters that are based on a treatment goal for the patient. The method further includes generating an output state of the patient based on the initial state of the patient and the plurality of treatment parameters, calculating an objective function based on the output state of the patient and the treatment goal of the patient, and updating one or more of the treatment parameters based on the objective function.

20 Claims, 7 Drawing Sheets

300

(51) Int. Cl.

| | |
|---|---|
| *A61C 9/00* | (2006.01) |
| *G06F 30/27* | (2020.01) |
| *G06T 19/20* | (2011.01) |
| *G16H 20/40* | (2018.01) |
| *G06F 111/10* | (2020.01) |

(52) U.S. Cl.
CPC .............. *G06T 19/20* (2013.01); *G16H 20/40* (2018.01); *G06F 2111/10* (2020.01); *G06T 2207/30004* (2013.01)

(58) Field of Classification Search
CPC ....... A61C 9/0046; A61C 7/002; G06T 19/20; G06T 2207/30004; G06F 2111/10; G06F 30/27
USPC ........................................................ 345/418
See application file for complete search history.

(56) References Cited

U.S. PATENT DOCUMENTS

| | | | |
|---|---|---|---|
| 6,227,851 B1 | 5/2001 | Chishti et al. |
| 6,299,440 B1 | 10/2001 | Phan et al. |
| 6,318,994 B1 | 11/2001 | Chishti et al. |
| 6,371,761 B1 | 4/2002 | Cheang et al. |
| 6,386,878 B1 | 5/2002 | Pavlovskaia et al. |
| 6,406,292 B1 | 6/2002 | Chishti et al. |
| 6,409,504 B1 | 6/2002 | Jones et al. |
| 6,457,972 B1 | 10/2002 | Chishti et al. |
| 6,488,499 B1 | 12/2002 | Miller |
| 6,514,074 B1 | 2/2003 | Chishti et al. |
| 6,554,611 B2 | 4/2003 | Chishti et al. |
| 6,582,229 B1 | 6/2003 | Miller et al. |
| 6,602,070 B2 | 8/2003 | Miller et al. |
| 6,621,491 B1 | 9/2003 | Baumrind et al. |
| 6,688,886 B2 | 2/2004 | Hughes et al. |
| 6,726,478 B1 | 4/2004 | Isiderio et al. |
| 6,729,876 B2 | 5/2004 | Chishti et al. |
| 6,739,869 B1 | 5/2004 | Taub et al. |
| 6,767,208 B2 | 7/2004 | Kaza |
| 6,783,360 B2 | 8/2004 | Chishti |
| 7,040,896 B2 | 5/2006 | Pavlovskaia et al. |
| 7,063,532 B1 | 6/2006 | Jones et al. |
| 7,074,038 B1 | 7/2006 | Miller |
| 7,074,039 B2 | 7/2006 | Kopelman et al. |
| 7,077,647 B2 | 7/2006 | Choi et al. |
| 7,108,508 B2 | 9/2006 | Hedge et al. |
| 7,134,874 B2 | 11/2006 | Chishti et al. |
| 7,156,661 B2 | 1/2007 | Choi et al. |
| 7,160,107 B2 | 1/2007 | Kopelman et al. |
| 7,241,142 B2 | 7/2007 | Abolfathi et al. |
| 7,293,988 B2 | 11/2007 | Wen |
| 7,309,230 B2 | 12/2007 | Wen |
| 7,357,634 B2 | 4/2008 | Knopp |
| 7,555,403 B2 | 6/2009 | Kopelman et al. |
| 7,637,740 B2 | 12/2009 | Knopp |
| 7,689,398 B2 | 3/2010 | Cheng et al. |
| 7,736,147 B2 | 6/2010 | Kaza et al. |
| 7,746,339 B2 | 6/2010 | Matov et al. |
| 7,844,356 B2 | 11/2010 | Matov et al. |
| 7,844,429 B2 | 11/2010 | Matov et al. |
| 7,865,259 B2 | 1/2011 | Kuo et al. |
| 7,878,804 B2 | 2/2011 | Korytov et al. |
| 7,880,751 B2 | 2/2011 | Kuo et al. |
| 7,904,308 B2 | 3/2011 | Arnone et al. |
| 7,930,189 B2 | 4/2011 | Kuo |
| 7,942,672 B2 | 5/2011 | Kuo |
| 7,970,627 B2 | 6/2011 | Kuo et al. |
| 7,970,628 B2 | 6/2011 | Kuo et al. |
| 8,038,444 B2 | 10/2011 | Kitching et al. |
| 8,044,954 B2 | 10/2011 | Kitching et al. |
| 8,075,306 B2 | 12/2011 | Kitching et al. |
| 8,092,215 B2 | 1/2012 | Stone-Collonge et al. |
| 8,099,268 B2 | 1/2012 | Kitching et al. |
| 8,108,189 B2 | 1/2012 | Chelnokov et al. |
| 8,126,726 B2 | 2/2012 | Matov et al. |
| 8,260,591 B2 | 9/2012 | Kass et al. |
| 8,275,180 B2 | 9/2012 | Kuo |
| 8,401,826 B2 | 3/2013 | Cheng et al. |
| 8,439,672 B2 | 5/2013 | Matov et al. |
| 8,562,338 B2 | 10/2013 | Kitching et al. |
| 8,591,225 B2 | 11/2013 | Wu et al. |
| 8,788,285 B2 | 7/2014 | Kuo |
| 8,843,381 B2 | 9/2014 | Kuo et al. |
| 8,874,452 B2 | 10/2014 | Kuo |
| 8,896,592 B2 | 11/2014 | Boltunov et al. |
| 8,930,219 B2 | 1/2015 | Trosien et al. |
| 9,037,439 B2 | 5/2015 | Kuo et al. |
| 9,060,829 B2 | 6/2015 | Sterental et al. |
| 9,125,709 B2 | 9/2015 | Matty |
| 9,211,166 B2 | 12/2015 | Kuo et al. |
| 9,220,580 B2 | 12/2015 | Borovinskih et al. |
| 9,364,296 B2 | 6/2016 | Kuo |
| 9,375,300 B2 | 6/2016 | Matov et al. |
| 9,414,897 B2 | 8/2016 | Wu et al. |
| 9,492,245 B2 | 11/2016 | Sherwood et al. |
| 9,642,678 B2 | 5/2017 | Kuo |
| 10,248,883 B2 | 4/2019 | Borovinskih et al. |
| 10,342,638 B2 | 7/2019 | Kitching et al. |
| 10,463,452 B2 | 11/2019 | Matov et al. |
| 10,595,966 B2 | 3/2020 | Carrier, Jr. et al. |
| 10,617,489 B2 | 4/2020 | Grove et al. |
| 10,722,328 B2 | 7/2020 | Velazquez et al. |
| 10,758,322 B2 | 9/2020 | Pokotilov et al. |
| 10,779,718 B2 | 9/2020 | Meyer et al. |
| 10,792,127 B2 | 10/2020 | Kopelman et al. |
| 10,828,130 B2 | 11/2020 | Pokotilov et al. |
| 10,835,349 B2 | 11/2020 | Cramer et al. |
| 10,973,611 B2 | 4/2021 | Pokotilov et al. |
| 10,996,813 B2 | 5/2021 | Makarenkova et al. |
| 10,997,727 B2 | 5/2021 | Xue et al. |
| 11,020,205 B2 | 6/2021 | Li et al. |
| 11,020,206 B2 | 6/2021 | Shi et al. |
| 11,026,766 B2 | 6/2021 | Chekh et al. |
| 11,033,359 B2 | 6/2021 | Velazquez et al. |
| 11,071,608 B2 | 7/2021 | Derakhshan et al. |
| 11,096,763 B2 | 8/2021 | Akopov et al. |
| 11,116,605 B2 | 9/2021 | Nyukhtikov et al. |
| 11,147,652 B2 | 10/2021 | Mason et al. |
| 11,151,753 B2 | 10/2021 | Gao et al. |
| 11,154,381 B2 | 10/2021 | Roschin et al. |
| 11,259,896 B2 | 3/2022 | Matov et al. |
| 11,357,598 B2 | 6/2022 | Cramer |
| 11,395,717 B2 | 7/2022 | Yuryev et al. |
| 11,432,908 B2 | 9/2022 | Kopelman et al. |
| 11,464,604 B2 | 10/2022 | Makarenkova et al. |
| 11,478,334 B2 | 10/2022 | Matov et al. |
| 11,484,389 B2 | 11/2022 | Sterental et al. |
| 11,521,732 B2 | 12/2022 | Levin et al. |
| 11,534,272 B2 | 12/2022 | Li et al. |
| 11,553,988 B2 * | 1/2023 | Mednikov ............... G06T 19/20 |
| 2003/0008259 A1 | 1/2003 | Kuo et al. |
| 2003/0143509 A1 | 7/2003 | Kopelman et al. |
| 2003/0207227 A1 | 11/2003 | Abolfathi |
| 2004/0137400 A1 | 7/2004 | Chishti et al. |
| 2004/0152036 A1 | 8/2004 | Abolfathi |
| 2004/0197728 A1 | 10/2004 | Abolfathi et al. |
| 2004/0259049 A1 | 12/2004 | Kopelman et al. |
| 2005/0182654 A1 | 8/2005 | Abolfathi et al. |
| 2005/0244791 A1 | 11/2005 | Davis et al. |
| 2006/0127836 A1 | 6/2006 | Wen |
| 2006/0127852 A1 | 6/2006 | Wen |
| 2006/0127854 A1 | 6/2006 | Wen |
| 2006/0275731 A1 | 12/2006 | Wen et al. |
| 2006/0275736 A1 | 12/2006 | Wen et al. |
| 2008/0306724 A1 | 12/2008 | Kitching et al. |
| 2010/0009308 A1 | 1/2010 | Wen et al. |
| 2010/0054411 A1 | 3/2010 | Nord et al. |
| 2010/0068672 A1 | 3/2010 | Arjomand et al. |
| 2010/0068676 A1 | 3/2010 | Mason et al. |
| 2010/0092907 A1 | 4/2010 | Knopp |
| 2010/0167243 A1 | 7/2010 | Spiridonov et al. |
| 2013/0204599 A1 | 8/2013 | Matov et al. |

(56) References Cited

U.S. PATENT DOCUMENTS

| | | | | |
|---|---|---|---|---|
| 2015/0265374 | A1* | 9/2015 | Masoud | G06V 40/171 |
| | | | | 382/128 |
| 2016/0310235 | A1 | 10/2016 | Derakhshan et al. | |
| 2017/0273760 | A1 | 9/2017 | Morton et al. | |
| 2018/0280118 | A1 | 10/2018 | Cramer | |
| 2019/0029784 | A1 | 1/2019 | Moalem et al. | |
| 2019/0328487 | A1 | 10/2019 | Levin et al. | |
| 2019/0328488 | A1 | 10/2019 | Levin et al. | |
| 2020/0107915 | A1 | 4/2020 | Roschin et al. | |
| 2020/0155274 | A1 | 5/2020 | Pimenov et al. | |
| 2020/0297458 | A1 | 9/2020 | Roschin et al. | |
| 2020/0306011 | A1 | 10/2020 | Chekhonin et al. | |
| 2020/0306012 | A1 | 10/2020 | Roschin et al. | |
| 2020/0360109 | A1 | 11/2020 | Gao et al. | |
| 2021/0073998 | A1 | 3/2021 | Brown et al. | |
| 2021/0134436 | A1 | 5/2021 | Meyer et al. | |
| 2021/0174477 | A1 | 6/2021 | Shi et al. | |
| 2021/0339049 | A1 | 11/2021 | Sjolund | |
| 2023/0132201 | A1* | 4/2023 | Chekh | G16H 50/50 |
| | | | | 345/419 |
| 2023/0268079 | A1* | 8/2023 | Lobsiger | G16H 20/30 |
| | | | | 382/128 |

OTHER PUBLICATIONS

Yuan P, Mai H, Li J, Ho DC, Lai Y, Liu S, Kim D, Xiong Z, Alfi DM, Teichgraeber JF, Gateno J. Design, development and clinical validation of computer-aided surgical simulation system for streamlined orthognathic surgical planning. International journal of computer assisted radiology and surgery. Dec. 2017; 12(12):21.*

Lee SJ, Yoo JY, Woo SY, Yang HJ, Kim JE, Huh KH, Lee SS, Heo MS, Hwang SJ, Yi WJ. A complete digital workflow for planning, simulation, and evaluation in orthognathic surgery. Journal of Clinical Medicine. Sep. 3, 2021;10(17):4000.*

Ma L, Xiao D, Kim D, Lian C, Kuang T, Liu Q, Deng H, Yang E, Liebschner MA, Gateno J, Xia JJ. Simulation of postoperative facial appearances via geometric deep learning for efficient orthognathic surgical planning. IEEE transactions on medical imaging. Jun. 3, 2022;42(2):336-45.*

Ma L, Kim D, Lian C, Xiao D, Kuang T, Liu Q, Lang Y, Deng HH, Gateno J, Wu Y, Yang E. Deep simulation of facial appearance changes following craniomaxillofacial bony movements in orthognathic surgical planning. InInternational Conference on Medical Image Computing and Computer-Assisted Intervention Sep. 21, 2021.*

Dorda, et al., "Differentiable Simulation for Outcome-driven Orthognathic Surgery Planning," Computer Graphics Forum, 2022, vol. 41 (8), pp. 1-9.

Kadlecek, et al., "Building Accurate Physics-based Face Models From Data," Proceedings of the ACM on Computer Graphics and Interactive Techniques, 2019, vol. 2 (2), 16 pages.

* cited by examiner

200

START

RECEIVE PATIENT DATA
(202)

RECEIVE A PLURALITY OF TREATMENT PARAMETERS
(204)

GENERATE AN OUTPUT STATE OF THE PATIENT BASED ON THE
INITIAL STATE OF THE PATIENT AND THE TREATMENT PARAMETERS
(206)

CALCULATE AN OBJECTIVE LOSS FUNCTION BASED ON THE
OUTPUT STATE OF THE PATIENT AND THE TREATMENT GOAL
(208)

UPDATE THE TREATMENT PARAMETERS BASED ON THE
OBJECTIVE LOSS FUNCTION
(210)

END

300

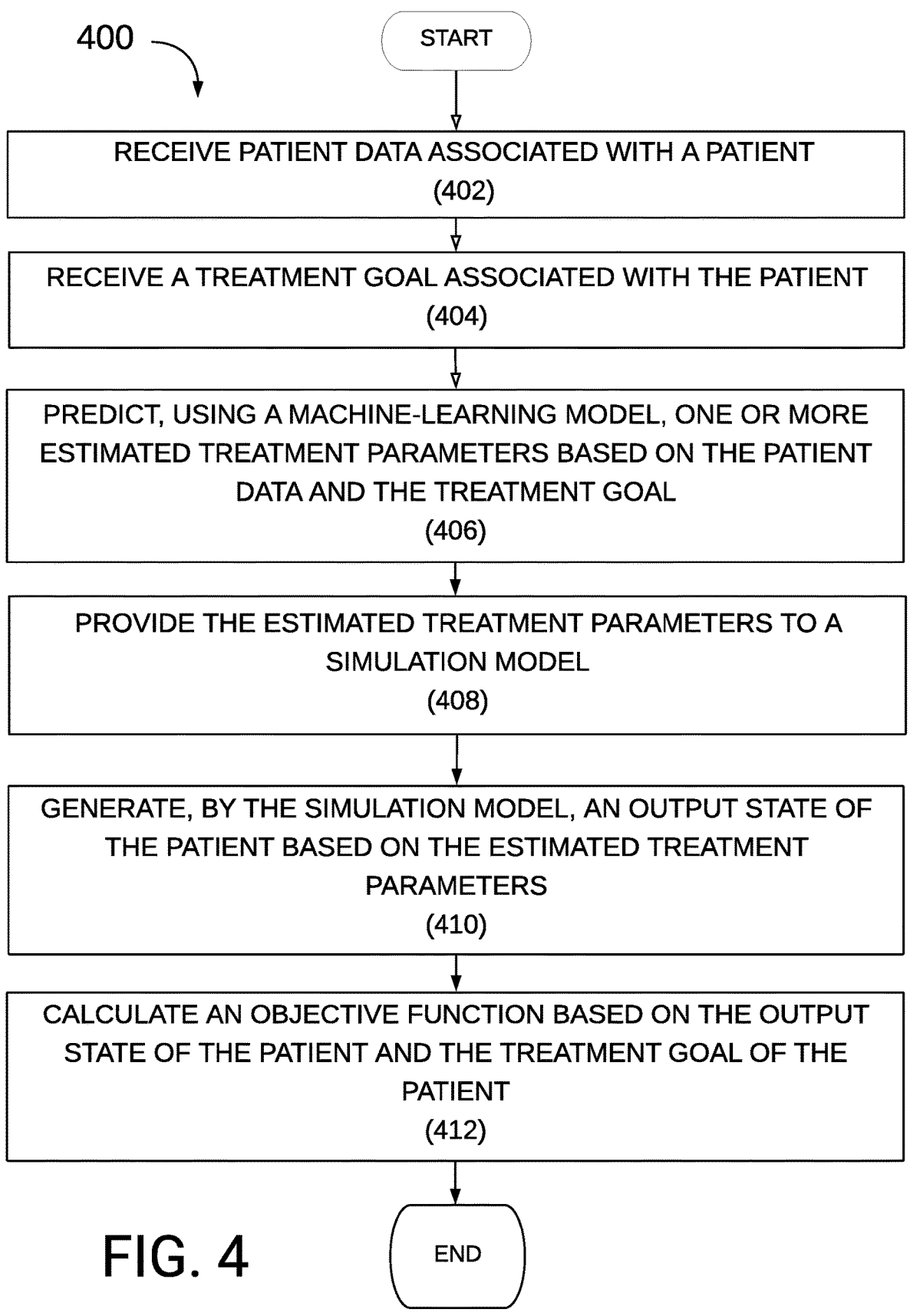

400

START

RECEIVE PATIENT DATA ASSOCIATED WITH A PATIENT
(402)

RECEIVE A TREATMENT GOAL ASSOCIATED WITH THE PATIENT
(404)

PREDICT, USING A MACHINE-LEARNING MODEL, ONE OR MORE
ESTIMATED TREATMENT PARAMETERS BASED ON THE PATIENT
DATA AND THE TREATMENT GOAL
(406)

PROVIDE THE ESTIMATED TREATMENT PARAMETERS TO A
SIMULATION MODEL
(408)

GENERATE, BY THE SIMULATION MODEL, AN OUTPUT STATE OF
THE PATIENT BASED ON THE ESTIMATED TREATMENT
PARAMETERS
(410)

CALCULATE AN OBJECTIVE FUNCTION BASED ON THE OUTPUT
STATE OF THE PATIENT AND THE TREATMENT GOAL OF THE
PATIENT
(412)

END

TREATMENT PARAMETER ESTIMATION USING ORTHOGNATHIC INFORMATION

RELATED APPLICATIONS

This patent application claims the benefit under 35 U.S.C. § 119(e) of U.S. Provisional Application No. 63/313,145, filed Feb. 23, 2022.

TECHNICAL FIELD

The present technology pertains to patient treatment modeling and in particular, to the use of treatment simulation models for predicting treatment outcomes. Additionally, the disclosed technology encompasses solutions for modeling how changes to specific treatment parameters can affect the ability for a given treatment plan to achieve patient goals.

BACKGROUND

A common objective of clinical interventions is to modify various structures of a patient's body, for example, to achieve improved performance and/or aesthetic appearance. In such instances, the goal of the clinician (e.g., doctor) is to take the patient from their current condition (initial state/condition) to a final condition (treatment outcome/goal). Depending on the type of procedure, there may be many ways to achieve the goal, e.g., through different implementations of a treatment plan. However, as the potential treatment plans become increasingly complex, it becomes difficult for an enterprise to sufficiently address communications with product providers.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which:

FIG. 4 is a flow diagram of an example process for training a machine-learning (ML) model to estimate treatment parameters in accordance with some examples.

DESCRIPTION OF EXAMPLE EMBODIMENTS

Figure 1:
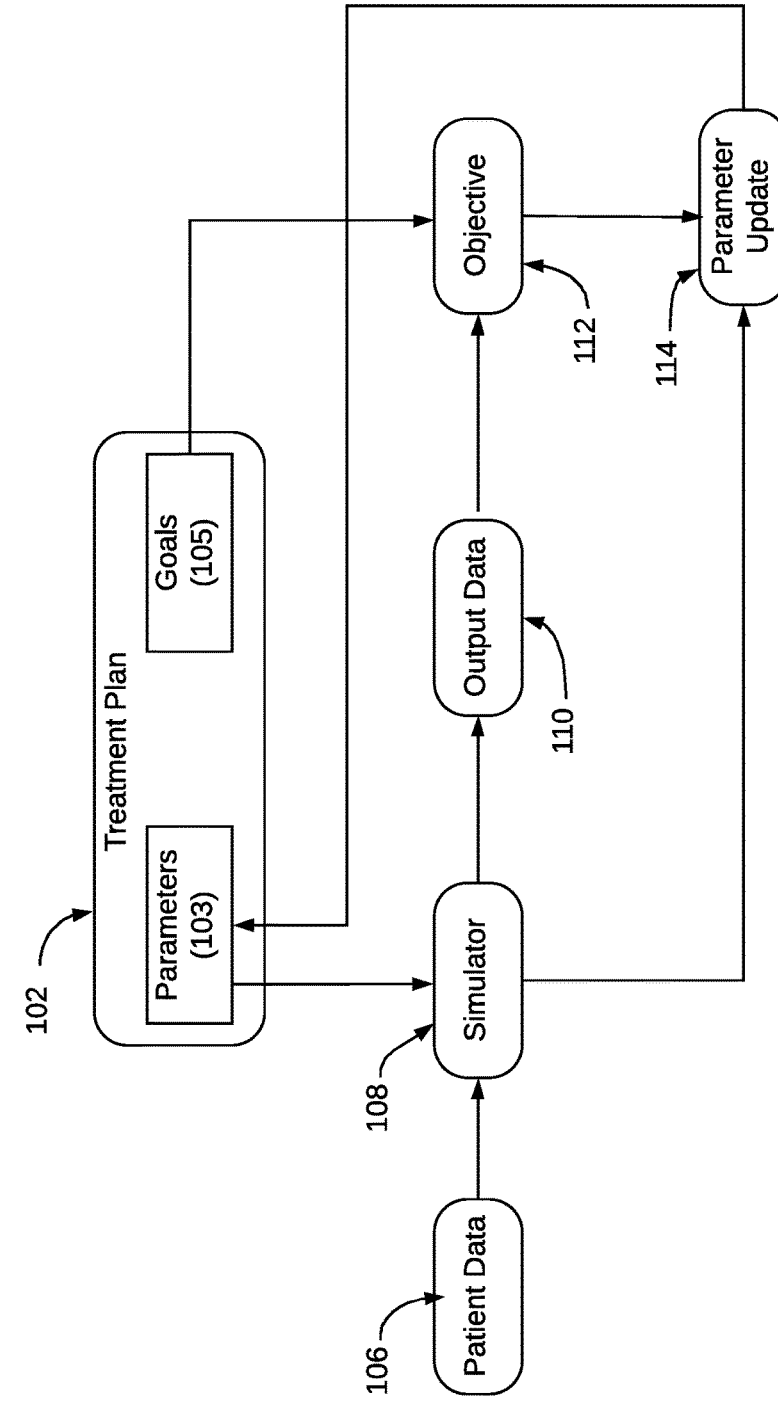
FIG. 1 illustrates a conceptual block diagram of an example differentiable simulator system that is configured to estimate treatment parameters based on a clinical goal, in accordance with some examples.

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure. Thus, the following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be references to the same embodiment or any embodiment; and, such references mean at least one of the embodiments.

Reference to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

Without intent to limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Additional features and advantages of the disclosure will be set forth in the description which follows, and in part will be obvious from the description, or can be learned by practice of the herein disclosed principles. The features and advantages of the disclosure can be realized and obtained by means of the instruments and combinations particularly pointed out in the appended claims. These and other features of the disclosure will become more fully apparent from the following description and appended claims, or can be learned by the practice of the principles set forth herein.

Overview

In some aspects, a computer-implemented method of the disclosed technology can include receiving patient data that includes information representing an initial state of a patient; receiving a plurality of treatment parameters, wherein the plurality of treatment parameters are based on a treatment goal for the patient; generating an output state of the patient based on the initial state of the patient and the treatment goal for the patient; calculating a loss function (or objective function) based on the output state of the patient and the treatment goal of the patient; and updating one or more of the treatment parameters based on the objective function.

A system of the disclosed technology can include at least one memory, and at least one processor coupled to the at least one memory, the at least one processor configured to: receive patient data, wherein the patient data includes information representing an initial state of a patient; receive a plurality of treatment parameters, wherein the plurality of treatment parameters are based on a treatment goal for the patient; generate an output state of the patient based on the initial state of the patient and the treatment goal for the patient; calculate an objective function (or loss function) based on the output state of the patient and the treatment goal of the patient; and update one or more of the treatment parameters based on the objective function.

A non-transitory computer-readable storage medium can include at least one instruction for causing a computer or processor to receive patient data, wherein the patient data includes information representing an initial state of a patient; receive a plurality of treatment parameters, wherein the plurality of treatment parameters are based on a treatment goal for the patient; generate an output state of the patient based on the initial state of the patient and the treatment goal for the patient; calculate an objective function based on the output state of the patient and the treatment goal of the patient; and update one or more of the treatment parameters based on the objective function.

In some aspects, a computer-implemented method of the disclosed technology can include steps for receiving, by a machine-learning (ML) model, patient data associated with a patient; receiving, by the ML model, a treatment goal associated with the patient; predicting, by the ML model, one or more estimated treatment parameters based on the patient data and the treatment goal; providing the one or more estimated treatment parameters to a simulation model; generating, by the simulation model, an output state of the patient based on the one or more estimated treatment parameters; and calculating an objective function based on the output state of the patient and the treatment goal of the patient.

A system of the disclosed technology can include at least one memory, and at least one processor coupled to the at least one memory, the at least one processor configured to: receive, by a machine-learning (ML) model, patient data associated with a patient; receive, by the ML model, a treatment goal associated with the patient; predict, by the ML model, one or more estimated treatment parameters based on the patient data and the treatment goal; provide the one or more estimated treatment parameters to a simulation model; generate, by the simulation model, an output state of the patient based on the one or more estimated treatment parameters; and calculate an objective function based on the output state of the patient and the treatment goal of the patient.

A non-transitory computer-readable storage medium (e.g., a program product) of the disclosed technology can include comprising at least one instruction for causing a computer or processor to: receive, by a machine-learning (ML) model, patient data associated with a patient; receive, by the ML model, a treatment goal associated with the patient; predict, by the ML model, one or more estimated treatment parameters based on the patient data and the treatment goal; provide the one or more estimated treatment parameters to a simulation model; generate, by the simulation model, an output state of the patient based on the one or more estimated treatment parameters; and calculate an objective function based on the output state of the patient and the treatment goal of the patient.

Description

As discussed previously, patient treatment plans can be used to achieve desired treatment outcomes or patient treatment goals. Depending on the treatment plan, different treatment parameters can be applied, and modified during the course of treatment to affect patient outcomes. Treatment parameters can include virtually any condition, variable and/or procedure that can affect treatment outcomes. By way of example, treatment parameters can include material parameters, including the composition, size and/or shape of implements used for administering treatment. In some approaches, treatment parameters may identify specific loci or regions (landmarks) of patient anatomy that are to be altered targeted by the applied treatment. Treatment parameters may also describe treatment techniques or procedures, such as the timing and/or order of applied procedures, etc. By way of example, orthodontic procedures can involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan. Treatment parameters in this context can include the type of appliances used (e.g., braces or shell aligners), material properties of the selected appliance (which affect forces exerted on each tooth), and/or treatment protocols, such as when the appliance is introduced into treatment, and/or a duration of use, etc. Treatment parameters are therefore crucial to achieving the intended treatment goals.

With the growing use of three-dimensional (3D) computer graphics and software in clinical applications it would be useful to use computational approaches to model the impact of various treatment parameters on clinical outcomes. In a similar manner, it would be useful to reverse-model treatment outcomes, for example, to ascertain what treatment parameters may be implemented to achieve a desired goal. However, due to the large number of potential treatment parameters attendant in even routine procedures, modeling approaches (e.g., that utilize naïve optimization strategies) are computationally intractable in most real-world scenarios.

Aspects of the disclosed technology provide solutions modeling treatment outcomes, and in particular for identifying and modifying specific treatment parameters for the purpose of achieving a clinical objective. Treatment outcomes can be predicted (modeled) using a differentiable simulator configured to receive input data representing a current patient state and treatment plan parameters, and to model the corresponding treatment outcome/s. In some aspects, the patient data can be representative of physical patient attributes. For example, patient data can include bio-mechanical models that represent the geometry of specific anatomical structures. In the orthodontic context, such models may include but are not limited to image data (e.g., photographs), cone beam computed tomography (CBCT) scan data, x-ray images, magnetic resonance imaging (MRI) data intra-oral scans, and/or face scans, etc.

The modeled patient outcomes can be used to compute an error function (or objective function) representing the difference between the desired goal and the modeled patient outcome. As such, in some approaches, the best patient treatment approach (e.g., the optimal combination of treatment parameters) are those that minimize variations between the modeled patient outcome and treatment goal, e.g., by minimizing the error function. As discussed in further detail below, differentiable simulation approaches (e.g., using the first derivative of the error function), can be used to identify treatment parameters that can be tuned/updated to most effectively minimize the error function.

In some implementations, machine-learning approaches may be used to identify/initialize treatment parameters, e.g., for the differentiable simulator. In such approaches, a machine-learning (ML) model trained to identify target treatment parameters (e.g., based on an intended goal) can be used to select/initialize treatment parameters for the differentiable simulator. As discussed in further detail below, parameter update techniques in which parameters are further tuned based on a derivative (e.g., a first derivative, or second derivative, etc.) of the error function (or objective function) can be used to further tune/update the ML selected treatment parameters.

Several of the provided examples relate to clinical interventions in the context of orthodontic treatment, however it is understood that the concepts disclosed herein may be applied in other clinical applications, without departing from the scope of the disclosed technology. For example, aspects of the disclosed technology may be applicable to various patient treatments, including surgical interventions that are used to modify various aspects of a patient's anatomy. By way of example, the disclosed approaches may be used in the context of orthognathic surgical interventions that are designed to alter patient jaw and/or face shapes, and the like.

FIG. 1 illustrates a conceptual block diagram of an example differentiable simulator system 100 that is configured to estimate treatment parameters based on a clinical goal, in accordance with some examples. Simulator system 100 includes a treatment plan 102 that includes treatment parameters 103, and treatment goals 105. As discussed above, treatment parameters 103 can include any metric or variable that can describe any aspect or characteristic of a patient-administered clinical intervention. Treatment goals 105 can include data describing an intended (or target) patient outcome. By way of example with respect to an orthodontic treatment context, treatment parameters 103 can include parameters describing the material composition and/or shape of aligner trays configured to reposition a patient's teeth in a predetermined manner. Treatment parameters 103 may also describe forces incident on different portions or locations of patient anatomy, such as forces imparted on individual teeth, or groups of teeth, as a result of tray configuration properties. In turn, treatment goals 105 can include data indicating the target dentition of the patient. By way of example, treatment goals 105 may include photographs and/or three-dimensional (3D) meshes (or other 3D model representations) of an intended or desired arrangement of the patient's teeth, and/or a desired aesthetic outcome.

In practice, treatment parameters 103 are provided to a simulator 108, in conjunction with patient data 106. The patient data 106 received by the simulator 108 can include any data representing a current or recent condition of the patient. For example, patient data can include measurements, or images representing a portion of the patient anatomy that is to be altered by the treatment intervention. In some aspects, the patient data 106 may be represented as a bio-mechanical model of the patient's anatomy. In the orthodontic context, for example, patient data can include images of teeth and/or facial features, including but not limited to digital images, inter-oral scans, cone beam computed tomography (CBCT) scans, x-ray images, and the like.

Using the received treatment parameters 103 and patient data 106, the simulator 108 can model expected patient outcomes (or output states), e.g., as represented by output data 110. In some aspects, the simulator 108 can be (or can utilize) a physics-based model, such as a bio-mechanical model that is configured to predict the outcome of treatment parameters on a provided patient state, as indicated by the patient data 106. By way of example, the simulator 108 can be configured to utilize a numerical method (e.g., such as the Finite Element Method (FEM)) to model the structural mechanics of a patient's anatomy when treated using interventions reflected by treatment parameters 103. Numerical modeling may be used to simulate the behavior of a patient's anatomy when treated using interventions reflected by treatment parameters 103. Examples of numerical methods that may be used in such modeling include finite element method (FEM), boundary element method (BEM), finite difference method (FDM), and discrete element method (DEM). Embodiments are discussed with reference to application of the finite element method (FEM), to finite element models, and to finite element analyses. However, it should be understood that any of the other possible types of numerical analysis and modeling may be performed in embodiments instead of FEM. Using the orthodontic example, the simulator 108 can be configured to model (predict) the movement of a patient's teeth in response to the application of an orthodontic liner. In this example, the treatment parameters 103 may include data reflecting the size, shape, and/or material characteristics of the liner, whereas patient data 106 may include data, such as images or 3D mesh models, reflecting the current positions and orientations of the patient's teeth and other oral structures.

The predicted impact of the applied treatment parameters 103 is reflected in output data 110 (or output state) generated by the simulator 108. Depending on the desired implementation, output data 110 can be (or can include) simulated post-treatment data in the form of a 3D mesh, or image data, for example, that reflects structural and/or aesthetic changes to the patient after intervention using the treatment parameters 103. The output data 110 can then be compared to the treatment goals 105 to determine/calculate an objective function 112 that represents a similarity between the post-treatment outcome (e.g., as output data 110) and the clinical goal of the patient (e.g., goals 105).

In some aspects, the objective function 112 can be used to identify specific treatment parameters (e.g., from among all the treatment parameters 103), that most significantly impact the post-treatment outcome. For example, a first derivative of the objective function 112 can be used to identify one or more treatment parameters that maximally contribute to a reduction in a magnitude associated with the objective function 112. Treatment parameters identified from the first derivative of the objective function (or loss function) 112 can be selected for modification/update, e.g., using a parameter update operation 114. In such instances, the previously applied treatment parameters 103 used by the simulator 108 can be modified based on the parameter selection performed using the objective function 112. Updated or tuned parameters can then be propagated back into the treatment plan 102, e.g., as an update to the treatment parameters 103 that are consumed by the simulator 108. The process of forward modeling the patient outcome (e.g., as reflected in the output data 110), and tuning the treatment parameters 103 consumed by the simulator 108 can be iterated until a satisfactory patient outcome is reached, i.e., until the treatment goal 105 is achieved.

In the context of an orthodontic intervention, for example, the simulator 108 can be used to predict the resulting geometry of a patient's teeth (e.g., as reflected in the output data 110), subsequent to an intervention utilizing treatment parameters (103), and based on the patient's current dentition (e.g., as reflected in the patient data 106). The output data 110 can then be used to determine (or compute) an objective function 112, to which a differential analysis can be applied. By way of example, differential analysis of the resulting objective function 112 may indicate that certain treatment parameters, such as aligner composition, may be more material to the achievement of the treatment goal 105, as compared with other/different treatment parameters, such as aligner geometry. Additionally, the derivatives can indicate, for each treatment parameter, a magnitude and a direction of update, e.g., to maximally reduce the loss (error). As such, by utilizing differential analysis of the objective (error) function 112, the treatment parameters 103 may be more efficiently tuned/updated, thereby improving the patient treatment outcome.

Figure 2:
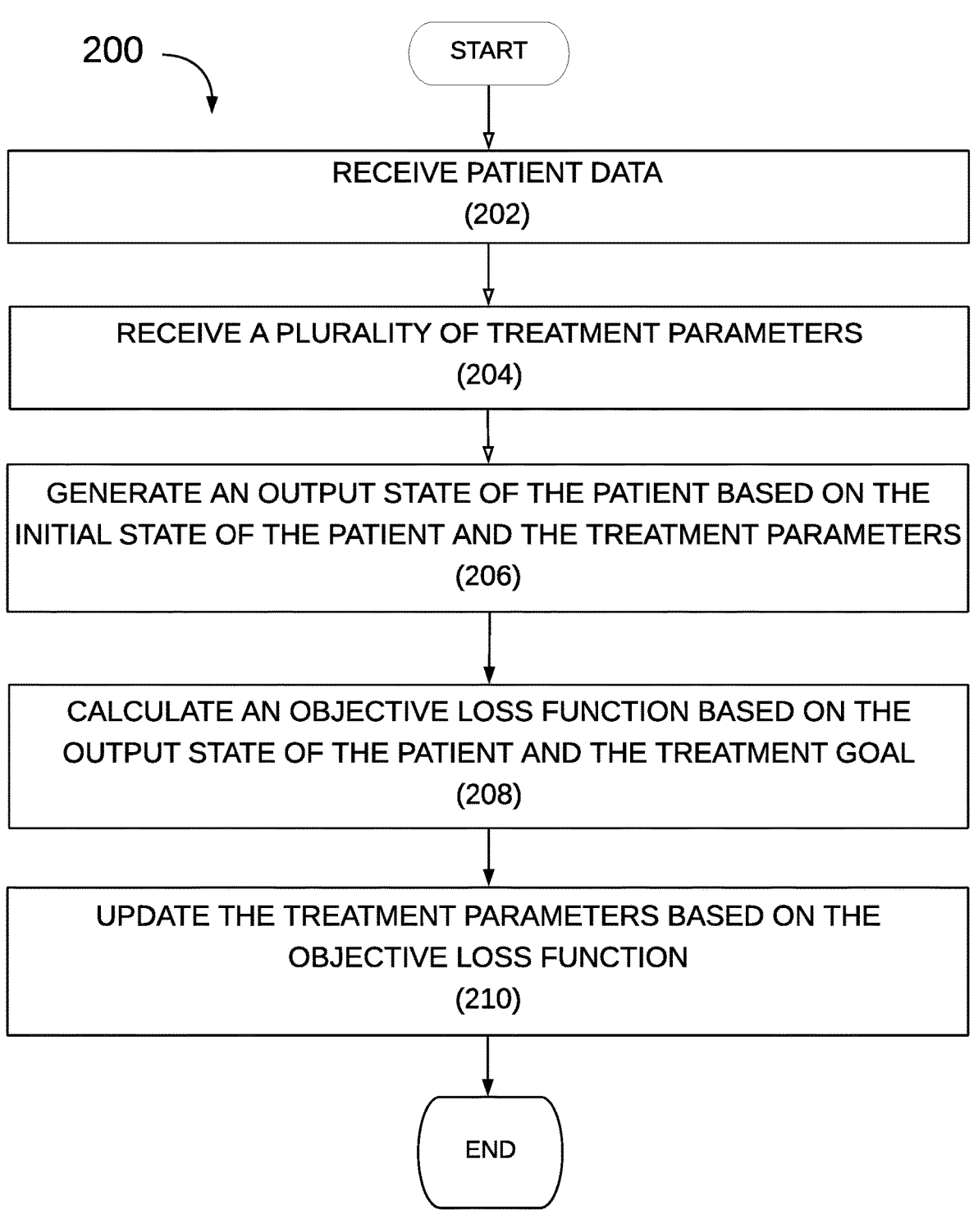
FIG. 2 is a flow diagram of an example process for performing treatment parameter estimation and tuning, in accordance with some examples.

FIG. 2 is a flow diagram of an example process 200 for performing treatment parameter estimation and tuning, in accordance with some examples. At step 202, patient data can be received, e.g., by a differentiable simulator, such as simulator 108, discussed above with respect to FIG. 1. The received patient data can represent an initial (or current) state of a patient, such as information describing a portion of the patient's anatomy. As discussed above, patient data can include bio-mechanical models that represent the geometry of specific anatomical structures. In the orthodontic context, such models may include but are not limited to image data (e.g., photographs), cone beam computed tomography (CBCT) scan data, x-ray images, magnetic resonance imaging (MRI) data, intra-oral scans, and/or face scans, etc.

At step 204, a plurality of treatment parameters can be received, e.g., by the differentiable simulator. As discussed above, treatment parameters can include material parameters, including the composition, size and/or shape of implements used for administering treatment. Treatment parameters may also describe treatment techniques or procedures, such as the timing and/or order of applied procedures, etc. By way of example, orthodontic procedures can involve repositioning a patient's teeth to a desired arrangement in order to correct malocclusions and/or improve aesthetics. To achieve these objectives, orthodontic appliances such as braces, shell aligners, and the like can be applied to the patient's teeth by an orthodontic practitioner. The appliance can be configured to exert force on one or more teeth in order to effect desired tooth movements according to a treatment plan. Treatment parameters in this context can include the type of appliances used (e.g., braces or shell aligners), material properties of the selected appliance (which affect forces exerted on each tooth), and/or treatment protocols, such as when the appliance is introduced into treatment, and/or a duration of use, etc.

At step 206, the process 200 includes generating an output state of the patient based on the initial state of the patient (e.g., based on the patient data), and the received treatment parameters. As discussed above with respect to FIG. 1, the output state can represent a simulation of the post-treatment outcome, e.g., that results from application of the treatment parameters. As such, the output state (or output data) can be (or can include) simulated post-treatment data in the form of a 3D mesh, or image data, for example, that reflects structural and/or aesthetic changes to the patient after applied intervention using the treatment parameters.

As discussed above, the output state can be an output generated by a simulation model, such as a differentiable simulator that is (or that includes) a physics-based model. By way of example, the simulator (or differentiable simulator) can be configured to utilize a finite element method (FEM) to model the structural mechanics of a patient's anatomy when treated using interventions reflected by the received treatment parameters.

At step 208, the process 200 includes calculating (or determining) an objective function based on the output state of the patient and the treatment goal. The objective function can represent a degree of similarity between the post-treatment outcome (e.g., as indicated by the output state/data) and the clinical goal for the patient. As discussed above, the loss function can be used to identify specific treatment parameters that most meaningfully impact the treatment outcome. For example, a first derivative of the objective function can be used to identify treatment parameters for modification/update, e.g., to better attain the patient's treatment goal.

At step 210, the process 200 includes updating one or more of the treatment parameters based on the objective function. In such approaches, certain (selected) previously applied treatment parameters can be modified based on the determined contribution to the objective function. For example, treatment parameters that contribute more meaningfully to the overall loss (or error) may be preferentially selected for modification/update, i.e., to improve outcomes of the administered treatment. The updated/tuned treatment parameters can then be propagated as inputs to the simulator.

In some aspects, treatment plan parameters may be initialized using machine-learning (ML) approaches. For example, treatment parameters may be provided as an output by an ML model trained to estimate/predict optimal treatment parameters given paired treatment goal and patient data inputs. Further details regarding the use of ML approaches to perform parameter estimation/initialization are provided with respect to FIGS. 3 and 4, below.

Figure 3:
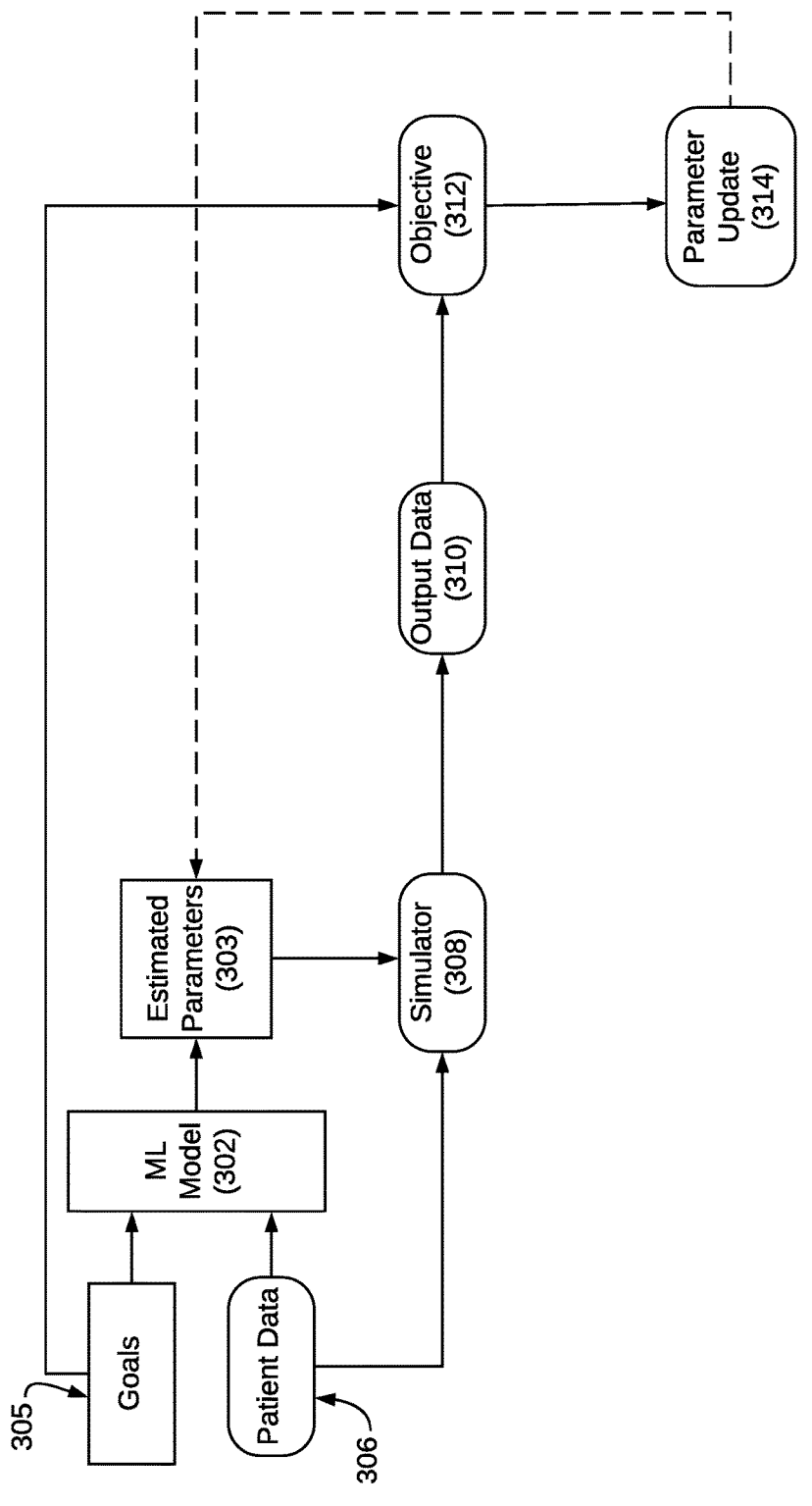
FIG. 3 illustrates a conceptual block diagram of an example differentiable simulator system in which treatment parameter initialization is performed using a machine-learning (ML) model, in accordance with some examples.

FIG. 3 illustrates a conceptual block diagram of an example differentiable simulator system 300 in which treatment parameter initialization is performed using a machine-learning (ML) model 302, in accordance with some examples. In the example of FIG. 3, ML model 302 is configured to predict/estimate treatment parameters 303, e.g., based on a paired input of treatment goals 305, and patient data 306. Similar to the examples discussed above with respect to FIG. 2, treatment goals can include any information representing a desired or intended patient outcome. By way of example, treatment goals may include representations of a target post-treatment outcome, including but not limited to images, and/or 3D mesh data, etc. Additionally, treatment goal data 305 may include other types of imaging data, including but not limited to cone beam computed tomography (CBCT) scan data, x-ray images, magnetic resonance imaging (Mill) data intra-oral scans, and/or face scans, etc. Similarly, the patient data 306 can include data representing a current (or most recent) condition of the patient, such as one or more regions of the patient's anatomy to be altered by the treatment plan. As such, the patient data may also include image data (e.g., photographs), cone beam computed tomography (CBCT) scan data, x-ray images, magnetic resonance imaging (Mill) data intra-oral scans, and/or face scans, etc.

Based on the received patient goal data 305 and the patient data 306, the ML model can predict/estimate initial treatment parameters 303 that are then provided to a simulator (e.g., a differentiable simulator 308). Similar to the process discussed above with respect to FIG. 1, the simulator 308 can use the received treatment parameters to model the impact of the applied treatment plan, and to output the predicted post-treatment results as output data 310. Depending on the desired implementation, the simulator 308 can be (or can utilize) a physics-based model, such as a bio-mechanical model configured to predict the outcome of treatment parameters on a provided patient state, as indicated by the patient data 306.

In some aspects, the output data 310 can be used to evaluate the simulated post-treatment result based on a similarity to the treatment objective, i.e., as defined by the treatment goals 305. As discussed above, this evaluation can be performed using an objective (error) function 312 that defines a disparity between the objective treatment goal 305, and the post-treatment patient result reflected in the output data 310. In some implementations, the objective error function 312 can be used to identify and update/tune selected parameters, as discussed above with respect to FIGS. 1 and 2. For example, using a differential analysis (e.g., by calculating a first derivative of the objective error function 312), treatment parameters that most impact the output data 310 can be identified. By updating/tuning these select parameters (e.g., in parameter update step 314), the input parameters 303 to the simulator 308 can be modified to better achieve the intended clinical outcome.

FIG. 4 is a flow diagram of an example process 400 for training a machine-learning (ML) model to estimate treatment parameters in accordance with some examples. The process 400 begins with step 402 in which patient data is received. The patient data can be representative of physical patient attributes. For example, patient data can include bio-mechanical models representing specific anatomical structures of the patient. By way of example, patient data may include, but is not limited to, image data (e.g., photographs), cone beam computed tomography (CBCT) scan data, x-ray images, magnetic resonance imaging (MRI) data intra-oral scans, and/or face scans, etc.

At step 404, the process 400 includes receiving a treatment goal associated with the patient. As discussed above, the treatment goal can include data specifying a desired/ target outcome for the treatment plan. Similar to the patient data, the treatment goal data can include, but is not limited to, image data (e.g., photographs), cone beam computed tomography (CBCT) scan data, x-ray images, magnetic resonance imaging (MM) data intra-oral scans, and/or face scans, etc.

At step 406, the process 400 can include predicting, using a ML model, one or more (estimated) treatment parameters, e.g., based on the patient data and the treatment goal. As discussed above, the ML model can be configured to predict optimal treatment parameters to achieve a desired patient objective.

At step 408, the process 400 can include providing the estimated treatment parameters to a simulation model, for example, that is configured to simulate post-treatment data for the patient, based on the applied treatment parameters. In some aspects, the simulation model can be (or can utilize) a physics-based model, such as a bio-mechanical model configured to predict the outcome of treatment parameters on a provided patient state, as indicated by the patient data received at step 402. By way of example, the simulation model can be configured to utilize a finite element method (FEM) to model the structural mechanics of a patient's anatomy when treated using interventions reflected by treatment parameters 103.

Using an orthodontic example, the simulation model can be configured to model (predict) the movement of a patient's teeth in response to the application of an orthodontic liner. In this example, the treatment parameters can include the size, shape, and/or material characteristics of the liner, whereas patient data may include images data and/or 3D mesh models reflecting the current positions and orientations of the patient's teeth and/or soft tissue structures.

In step 410, the process 400 includes generating an output state of the patient based on the initial state of the patient (e.g., based on the patient data), and the received treatment parameters. As discussed above, the output state can represent a simulation of the post-treatment outcome, e.g., that results from application of the treatment parameters. As such, the output state (or output data) can include simulated post-treatment data in the form of a 3D mesh, or image data, for example, that reflects structural and/or aesthetic changes to the patient after applied intervention using the treatment parameters.

At step 412, the process 400 includes calculating an objective function (also: loss function) based on the output state of the patient and the treatment goal of the patient. The objective function can be used to determine a success (or failure) of the applied treatment, for example, by representing a disparity between the post-treatment patient state and the treatment goal. In some aspects, the objective loss can be used to update one or more weights of the machine-learning model in order to perform training. In some aspects, a derivative of the objective function (loss function) may be used to determine a magnitude and direction (sign) of ML model weights to be updated. Through training, the computed objective function can be used to improve the ML model predictions about future treatment parameters. Once trained and deployed into production, in some aspects, the loss function may be used to further update treatment parameters that are provided to the simulation model, e.g., in instances where additional simulation iterations are desired. By way of example, differential analysis techniques may be used to identify/select specific treatment parameters for updating/tuning, which can then be used to perform additional treatment simulation.

Figure 5:
FIG. 5 illustrates an example of a CT scan of patient teeth, in accordance with some examples.

FIG. 5 shows an exemplary diagram 500 of a CT scan of teeth. In this embodiment, the roots are derived directly from a high-resolution CBCT scan of the patient. Scanned roots can then be applied to crowns derived from an impression, or used with the existing crowns extracted from Cone Beam Computed Tomography (CBCT) data. A CBCT single scan gives 3D data and multiple forms of X-ray-like data. PVS impressions are avoided.

In one embodiment, a cone beam x-ray source and a 2D area detector scans the patient's dental anatomy, preferably over a 360 degree angular range and along its entire length, by any one of various methods wherein the position of the area detector is fixed relative to the source, and relative rotational and translational movement between the source and object provides the scanning (irradiation of the object by radiation energy). As a result of the relative movement of the cone beam source to a plurality of source positions (i.e., "views") along the scan path, the detector acquires a corresponding plurality of sequential sets of cone beam projection data (also referred to herein as cone beam data or projection data), each set of cone beam data being representative of x-ray attenuation caused by the object at a respective one of the source positions.

Figure 6:
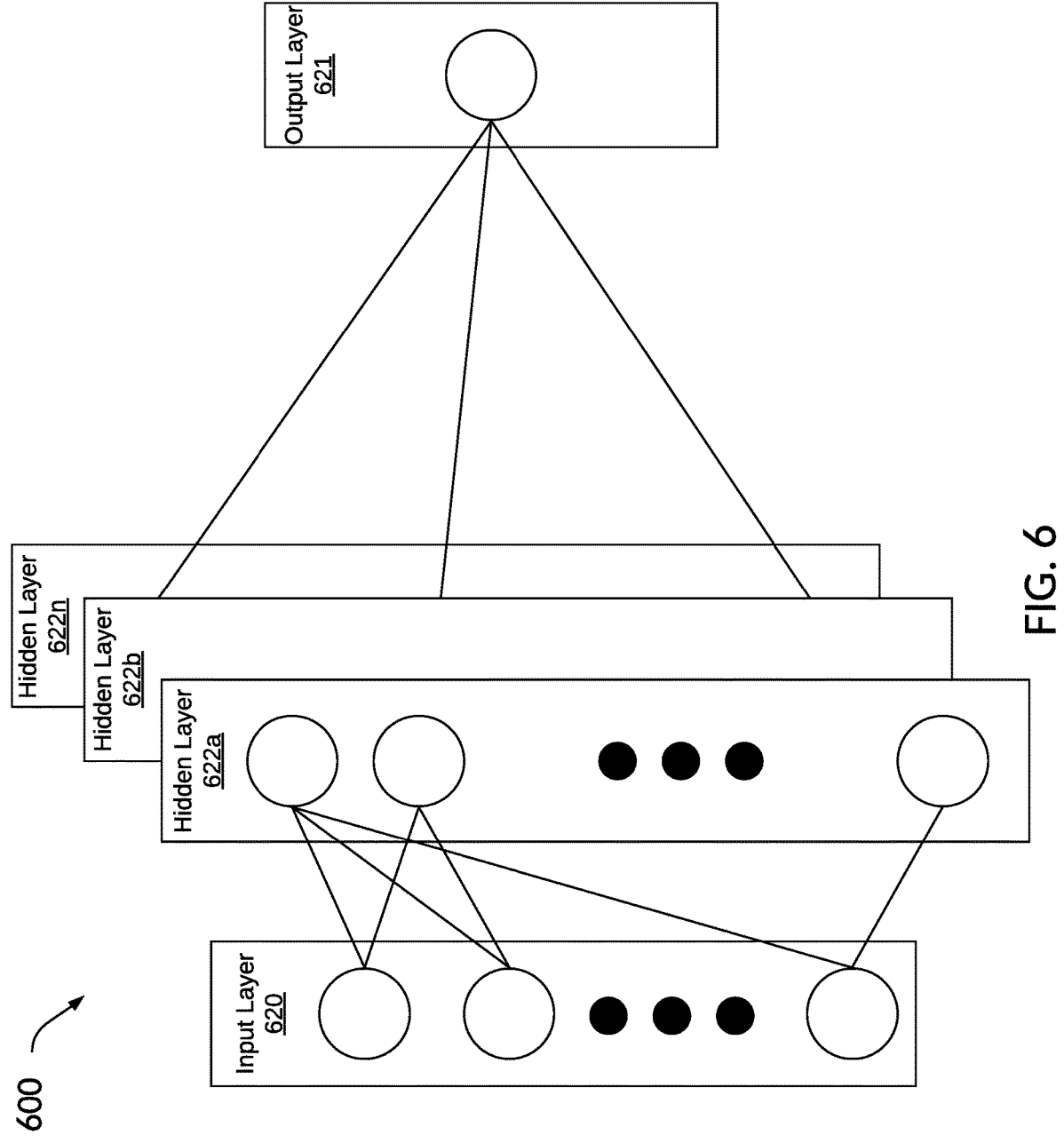
FIG. 6 illustrates an example of a deep learning neural network that can be implemented to identify initial treatment parameters used by a differentiable simulator, in accordance with some examples.

The disclosure now turns to a further discussion of models that can be used through the environments and techniques described herein. Specifically, FIG. 6 is an illustrative example of a deep learning neural network 600 that can be implemented to perform treatment parameter estimation. As discussed above, an input layer 620 can be configured to receive patient data and/or data relating to target treatment goals. The neural network 600 includes multiple hidden layers 622a, 622b, through 622n. The hidden layers 622a, 622b, through 622n include "n" number of hidden layers, where "n" is an integer greater than or equal to one. The number of hidden layers can be made to include as many layers as needed for the given application. The neural network 600 further includes an output layer 621 that provides an output resulting from the processing performed by the hidden layers 622a, 622b, through 622n. In one illustrative example, the output layer 621 can provide estimated treatment parameters (e.g., estimated parameters 303), that can be used/ingested by a differential simulator to estimate a patient treatment outcome.

The neural network 600 is a multi-layer neural network of interconnected nodes. Each node can represent a piece of information. Information associated with the nodes is shared among the different layers and each layer retains information as information is processed. In some cases, the neural network 600 can include a feed-forward network, in which case there are no feedback connections where outputs of the network are fed back into itself. In some cases, the neural network 600 can include a recurrent neural network, which can have loops that allow information to be carried across nodes while reading in input.

Information can be exchanged between nodes through node-to-node interconnections between the various layers. Nodes of the input layer 620 can activate a set of nodes in the first hidden layer 622a. For example, as shown, each of the input nodes of the input layer 620 is connected to each of the nodes of the first hidden layer 622a. The nodes of the first hidden layer 622a can transform the information of each input node by applying activation functions to the input node information. The information derived from the transformation can then be passed to and can activate the nodes of the next hidden layer 622b, which can perform their own designated functions. Example functions include convolutional, up-sampling, data transformation, and/or any other suitable functions. The output of the hidden layer 622b can then activate nodes of the next hidden layer, and so on. The output of the last hidden layer 622n can activate one or more nodes of the output layer 621, at which an output is provided. In some cases, while nodes (e.g., node 626) in the neural network 600 are shown as having multiple output lines, a node can have a single output and all lines shown as being output from a node represent the same output value.

In some cases, each node or interconnection between nodes can have a weight that is a set of parameters derived from the training of the neural network 600. Once the neural network 600 is trained, it can be referred to as a trained neural network, which can be used to classify one or more activities. For example, an interconnection between nodes can represent a piece of information learned about the interconnected nodes. The interconnection can have a tunable numeric weight that can be tuned (e.g., based on a training dataset), allowing the neural network 600 to be adaptive to inputs and able to learn as more and more data is processed.

The neural network 600 is pre-trained to process the features from the data in the input layer 620 using the different hidden layers 622a, 622b, through 622n in order to provide the output through the output layer 621.

In some cases, the neural network 600 can adjust the weights of the nodes using a training process called backpropagation. As noted above, a backpropagation process can include a forward pass, a loss function, a backward pass, and a weight update. The forward pass, loss function, backward pass, and parameter update is performed for one training iteration. The process can be repeated for a certain number of iterations for each set of training data until the neural network 600 is trained well enough so that the weights of the layers are accurately tuned.

As noted above, for a first training iteration for the neural network 600, the output will likely include values that do not give preference to any particular class due to the weights being randomly selected at initialization. For example, if the output is a vector with probabilities that the object includes different classes, the probability value for each of the different classes may be equal or at least very similar (e.g., for ten possible classes, each class may have a probability value of 0.1). With the initial weights, the neural network 600 is unable to determine low level features and thus cannot make an accurate determination of what the classification of the object might be. A loss function can be used to analyze error in the output. Any suitable loss function definition can be used, such as a Cross-Entropy loss. Another example of a loss function includes the mean squared error (MSE), defined as $E\_total=\Sigma(\frac{1}{2}(target-output)^2)$. The loss can be set to be equal to the value of E_total.

The loss (or error) will be high for the first training images since the actual values will be much different than the predicted output. The goal of training is to minimize the amount of loss so that the predicted output is the same as the training label. The neural network 600 can perform a backward pass by determining which inputs (weights) most contributed to the loss of the network, and can adjust the weights so that the loss decreases and is eventually minimized. A derivative of the loss with respect to the weights (denoted as dL/dW, where W are the weights at a particular layer) can be computed to determine the weights that contributed most to the loss of the network. After the derivative is computed, a weight update can be performed by updating all the weights of the filters. For example, the weights can be updated so that they change in the opposite direction of the gradient. The weight update can be denoted as $w=w\_i-\eta\ dL/dW$, where w denotes a weight, wi denotes the initial weight, and $\eta$ denotes a learning rate. The learning rate can be set to any suitable value, with a high learning rate including larger weight updates and a lower value indicating smaller weight updates.

The neural network 600 can include any suitable deep network. One example includes a convolutional neural network (CNN), which includes an input layer and an output layer, with multiple hidden layers between the input and out layers. The hidden layers of a CNN include a series of convolutional, nonlinear, pooling (for downsampling), and fully connected layers. The neural network 600 can include any other deep network other than a CNN, such as an autoencoder, a deep belief nets (DBNs), a Recurrent Neural Networks (RNNs), among others.

As understood by those of skill in the art, machine-learning based classification techniques can vary depending on the desired implementation. For example, machine-learning classification schemes can utilize one or more of the following, alone or in combination: hidden Markov models; recurrent neural networks; convolutional neural networks (CNNs); deep learning; Bayesian symbolic methods; generative adversarial networks (GANs); support vector machines; image registration methods; applicable rule-based system. Where regression algorithms are used, they may include but are not limited to: a Stochastic Gradient Descent Regressor, and/or a Passive Aggressive Regressor, etc.

Machine learning classification models can also be based on clustering algorithms (e.g., a Mini-batch K-means clustering algorithm), a recommendation algorithm (e.g., a Miniwise Hashing algorithm, or Euclidean Locality-Sensitive Hashing (LSH) algorithm), and/or an anomaly detection algorithm, such as a Local outlier factor. Additionally, machine-learning models can employ a dimensionality reduction approach, such as, one or more of: a Mini-batch Dictionary Learning algorithm, an Incremental Principal Component Analysis (PCA) algorithm, a Latent Dirichlet Allocation algorithm, and/or a Mini-batch K-means algorithm, etc.

Figure 7:
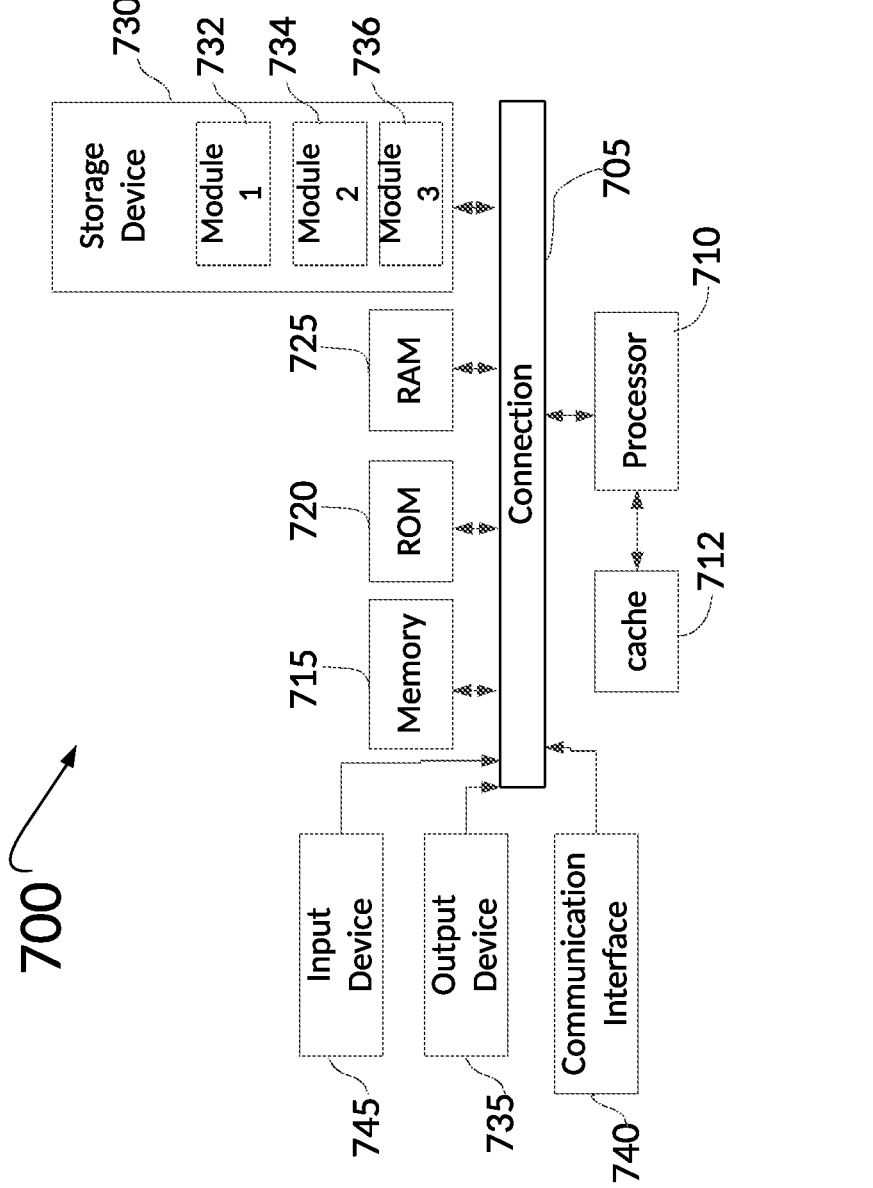
FIG. 7 illustrates an example computing system, in accordance with some examples.

The disclosure now turns to FIG. 7 which illustrates an example of a processor-based computing system 700 wherein the components of the system are in electrical communication with each other using a bus 705. The computing system 700 can include a processing unit (CPU or processor) 710 and a system bus 705 that may couple various system components including the system memory 715, such as read only memory (ROM) 720 and random-access memory (RAM) 725, to the processor 710. The computing system 700 can include a cache 712 of high-speed memory connected directly with, in close proximity to, or integrated as part of the processor 710. The computing system 700 can copy data from the memory 715, ROM 720, RAM 725, and/or storage device 730 to the cache 712 for quick access by the processor 710. In this way, the cache 712 can provide a performance boost that avoids processor delays while waiting for data. These and other modules can control the processor 710 to perform various actions. Other system memory 715 may be available for use as well. The memory 715 can include multiple different types of memory with different performance characteristics. The processor 710 can include any general-purpose processor and a hardware module or software module, such as module 1 732, module 2 734, and module 3 736 stored in the storage device 730, configured to control the processor 710 as well as a special-purpose processor where software instructions are incorporated into the actual processor design. The processor 710 may essentially be a completely self-contained computing system, containing multiple cores or processors, a bus, memory controller, cache, etc. A multi-core processor may be symmetric or asymmetric.

To enable user interaction with the computing system 700, an input device 745 can represent any number of input mechanisms, such as a microphone for speech, a touch-protected screen for gesture or graphical input, keyboard, mouse, motion input, speech and so forth. An output device 735 can also be one or more of a number of output mechanisms known to those of skill in the art. In some instances, multimodal systems can enable a user to provide multiple types of input to communicate with the computing system 700. The communications interface 740 can govern and manage the user input and system output. There may be no restriction on operating on any particular hardware arrangement and therefore the basic features here may easily be substituted for improved hardware or firmware arrangements as they are developed.

The storage device 730 can be a non-volatile memory and can be a hard disk or other types of computer readable media which can store data that are accessible by a computer, such as magnetic cassettes, flash memory cards, solid state memory devices, digital versatile disks, cartridges, random access memory, read only memory, and hybrids thereof.

As discussed above, the storage device 730 can include the software modules 732, 734, 736 for controlling the processor 710. Other hardware or software modules are contemplated. The storage device 730 can be connected to the system bus 705. In some embodiments, a hardware module that performs a particular function can include a software component stored in a computer-readable medium in connection with the necessary hardware components, such as the processor 710, bus 705, output device 735, and so forth, to carry out the function. For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can comprise, for example, instructions and data which cause or otherwise configure a general purpose computer, special purpose computer, or special purpose processing device to perform a certain function or group of functions. Portions of computer resources used can be accessible over a network. The computer executable instructions may be, for example, binaries, intermediate format instructions such as assembly language, firmware, or source code. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can comprise hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are means for providing the functions described in these disclosures.

Although a variety of examples and other information was used to explain aspects within the scope of the appended claims, no limitation of the claims should be implied based on particular features or arrangements in such examples, as one of ordinary skill would be able to use these examples to derive a wide variety of implementations. Further and although some subject matter may have been described in language specific to examples of structural features and/or method steps, it is to be understood that the subject matter defined in the appended claims is not necessarily limited to these described features or acts. For example, such functionality can be distributed differently or performed in components other than those identified herein. Rather, the described features and steps are disclosed as examples of components of systems and methods within the scope of the appended claims.

Claim language reciting "at least one of" refers to at least one of a set and indicates that one member of the set or multiple members of the set satisfy the claim. For example, claim language reciting "at least one of A and B" means A, B, or A and B.

What is claimed is:

1. A computer-implemented method comprising:

receiving orthognathic patient data, wherein the orthognathic patient data comprises information representing an initial state of a patient, the information comprising a first three-dimensional model reflecting current positions and orientations of teeth and other oral structures of the patient;

receiving a plurality of treatment parameters for an orthodontic treatment plan, wherein the plurality of treatment parameters are based on a treatment goal for the patient, wherein the treatment goal comprises a second three-dimensional model of a target arrangement of the teeth of the patient, and wherein the plurality of treatment parameters comprise at least one of:

a type of orthodontic appliance;

a material composition of one or more orthodontic appliances;

one or more orthodontic treatment protocols;

shapes of the one or more orthodontic appliances; or forces incident on individual teeth or groups of teeth of the patient;

predicting an output state of the patient comprising a post-treatment arrangement of the teeth of the patient in the form of a third three-dimensional model based on processing the initial state of the patient and the plurality of treatment parameters using a simulator;

calculating an objective function based on differences between the output state of the patient and the treatment goal of the patient; and updating one or more of the treatment parameters based on the objective function to minimize a difference between the predicted output state and the treatment goal of the patient.

2. The computer-implemented method of claim 1, wherein the orthognathic patient data comprises one or more surface images of the patient's face.

3. The computer-implemented method of claim 1, wherein the orthognathic patient data comprises one or more three-dimensional models of the patient's face.

4. The computer-implemented method of claim 1, wherein the orthognathic patient data comprises one or more three-dimensional models of the patient's jaw bone.

5. The computer-implemented method of claim 1, wherein the treatment parameters comprise one or more facial landmarks associated with the patient.

6. The computer-implemented method of claim 1, wherein updating the one or more treatment parameters further comprises:

identifying the one or more treatment parameters based on a derivative of the objective function.

7. The computer-implemented method of claim 1, wherein predicting the output state of the patient further comprises:

providing the orthognathic patient data and the plurality of treatment parameters to a simulation model of the simulator, wherein the simulation model comprises a numerical model.

8. The computer-implemented method of claim 7, wherein the numerical model comprises a bio-mechanical model.

9. The computer-implemented method of claim 1, wherein the third three-dimensional model is a three-dimensional (3D) mesh.

10. A system comprising:

a memory; and a processor operatively coupled with the memory, the processor to:

receive orthognathic patient data comprising information representing an initial state of a patient, the information comprising a first three-dimensional model reflecting current positions and orientations of teeth and other oral structures of the patient;

receive a plurality of treatment parameters for an orthodontic treatment plan, wherein the plurality of treatment parameters are based on a treatment goal for the patient, wherein the treatment goal comprises a second three-dimensional model of a target arrangement of the teeth of the patient, and wherein the plurality of treatment parameters comprise at least one of:

a type of orthodontic appliance;

a material composition of one or more orthodontic appliances;

one or more orthodontic treatment protocols;

shapes of the one or more orthodontic appliances; or forces incident on individual teeth or groups of teeth of the patient;

predict an output state of the patient comprising a post-treatment arrangement of the teeth of the patient in the form of a third three-dimensional model based on the initial state of the patient and the plurality of treatment parameters using a simulator;

calculate an objective function based on differences between the output state of the patient and the treatment goal of the patient; and update one or more of the treatment parameters based on the objective function to minimize a difference between the predicted output state and the treatment goal of the patient.

11. The system of claim 10, wherein the orthognathic patient data comprises one or more surface images of the patient's face.

12. The system of claim 10, wherein the orthognathic patient data comprises one or more three-dimensional models of the patient's face.

13. The system of claim 10, wherein the orthognathic patient data comprises one or more three-dimensional models of the patient's jaw bone.

14. The system of claim 10, wherein the treatment parameters comprise one or more facial landmarks associated with the patient.

15. The system of claim 10, wherein the processor is further to:

identify the one or more treatment parameters based on a derivative of the objective function.

16. The system of claim 10, wherein the processor is further to:

provide the orthognathic patient data and the plurality of treatment parameters to a simulation model of the simulator, wherein the simulation model comprises a numerical model.

17. The system of claim 16, wherein the numerical model comprises a bio-mechanical model.

18. The system of claim 10, wherein the third three-dimensional model is a three-dimensional (3D) mesh.

19. A non-transitory computer readable medium comprising instructions that, when executed by a processor, cause the processor to perform operations comprising:

receiving orthognathic patient data comprising information representing an initial state of a patient, the information comprising a first three-dimensional model reflecting current positions and orientations of teeth and other oral structures of the patient based on intraoral scans of the patient;

receiving a plurality of treatment parameters for an orthodontic treatment plan, wherein the plurality of treatment parameters are based on a treatment goal for the patient, wherein the treatment goal comprises a second three-dimensional model of a target arrangement of the teeth of the patient, and wherein the plurality of treatment parameters comprise at least one of:

a type of orthodontic appliance;

a material composition of one or more orthodontic appliances;

one or more orthodontic treatment protocols;

shapes of the one or more orthodontic appliances; or forces incident on individual teeth or groups of teeth of the patient;

predicting an output state of the patient comprising a post-treatment arrangement of the teeth of the patient in the form of a third three-dimensional model based on processing the initial state of the patient and the plurality of treatment parameters using a simulator;

calculating an objective function based on differences between the output state of the patient and the treatment goal of the patient; and updating one or more of the treatment parameters based on the objective function to minimize a difference between the predicted output state and the treatment goal of the patient.

20. The non-transitory computer readable medium of claim 19, wherein predicting the output state of the patient comprises:

providing the orthognathic patient data and the plurality of treatment parameters to a simulation model of the simulator, wherein the simulation model comprises a numerical model that generates the output state of the patient.

* * * * *